(12) United States Patent
Wagh et al.

(10) Patent No.: US 9,149,482 B2
(45) Date of Patent: Oct. 6, 2015

(54) PHARMACEUTICAL FORMULATION OF CEFIXIME FOR ENHANCED BIOAVAILABILITY

(75) Inventors: Sanjay Wagh, Pune (IN); Hidaytulla Aga, Pune (IN); Makarand Avachat, Pune (IN); Himadri Sen, Pune (IN)

(73) Assignee: Lupin Ltd., Mumbai (IN)

( * ) Notice: Subject to any disclaimer, the term of this patent is extended or adjusted under 35 U.S.C. 154(b) by 1219 days.

(21) Appl. No.: 11/579,988

(22) PCT Filed: May 10, 2004

(86) PCT No.: PCT/IN2004/000128
§ 371 (c)(1),
(2), (4) Date: Jun. 25, 2007

(87) PCT Pub. No.: WO2005/107703
PCT Pub. Date: Nov. 17, 2005

(65) Prior Publication Data
US 2007/0286901 A1      Dec. 13, 2007

(51) Int. Cl.
  *A61K 9/20*      (2006.01)
  *A61K 31/545*    (2006.01)
  *A61K 31/546*    (2006.01)
  *A61K 9/00*      (2006.01)

(52) U.S. Cl.
  CPC .............. *A61K 31/546* (2013.01); *A61K 9/0056* (2013.01)

(58) Field of Classification Search
  None
  See application file for complete search history.

(56) References Cited

U.S. PATENT DOCUMENTS

| 4,409,214 | A  |   | 10/1983 | Takaya et al. |
| 4,525,341 | A  | * | 6/1985  | Deihl ............................. 424/43 |
| 4,569,852 | A  | * | 2/1986  | Yang ............................. 426/534 |
| 5,514,383 | A  | * | 5/1996  | Laly et al. .................... 424/464 |
| 5,776,926 | A  |   | 7/1998  | Bolz et al. |
| 6,248,363 | B1 | * | 6/2001  | Patel et al. ................... 424/497 |
| 6,423,341 | B1 | * | 7/2002  | Yamaguchi .................. 424/465 |
| 6,740,339 | B1 | * | 5/2004  | Ohkouchi et al. ........... 424/464 |
| 2004/0006111 | A1 | * | 1/2004 | Widder et al. ................ 514/338 |

FOREIGN PATENT DOCUMENTS

| EP | 0 890 359 A1  |   | 1/1999  |
| FR | 2 814 679     |   | 4/2002  |
| JP | 200443475     | * | 2/2004  |
| WO | 98/46213      |   | 10/1998 |
| WO | 2005/107703 A1|   | 11/2005 |

OTHER PUBLICATIONS

Faulkner et al. "Bioequivalency of solid oral dosage forms of cefixime" International Journal of Pharmaceutics 43 (1988) p. 53-58.
Kees et al. "Relative Bioavailability of Three Cefixime Formulations" Arzneim-Forsch./Drug Res. 40 (I) Nr. 3 (1990) p. 293-297.

* cited by examiner

*Primary Examiner* — Tigabu Kassa
(74) *Attorney, Agent, or Firm* — Leydig, Voit & Mayer, Ltd.

(57) ABSTRACT

A chewable tablet comprising Cefixime having a mean particle size between 20μ and 120μ wherein the said composition demonstrates bioequivalence to a suspension of Cefixime trihydrate. The process of preparation of the chewable tablet comprises the steps of optionally micronizing Cefixime such that the mean particle size of the Cefixime particles is between 20μ and 120μ, blending with other excipients, roll compaction, milling to form granules, blending to form a secondary blend and compression of the secondary blend to form tablets.

16 Claims, No Drawings

PHARMACEUTICAL FORMULATION OF CEFIXIME FOR ENHANCED BIOAVAILABILITY

FIELD OF THE INVENTION

The present invention relates to novel pharmaceutical formulation comprising Cefixime.

BACKGROUND OF THE INVENTION

Cefixime is a semi synthetic cephalosporin antibiotic for oral administration. It was first disclosed in U.S. Pat. No. 4,409,214 by Fujisawa Corporation, Japan. It is indicated for the treatment of infections caused by various gram—positive and gram—negative organisms chiefly uncomplicated urinary tract infections caused by *E. coli* and *P. mirabilis*, otitis media caused by *H. influenza, M. catarrhalis* and *S. pyogenes*, acute bronchitis and exacerbations of chronic bronchitis caused by *S. pneumonia* and *H. influenza*. It is also indicated for uncomplicated gonorrhea caused by *N. gonorrhea*. It is one of the most prescribed drugs for pediatric use.

Cefixime is currently available in a number of different formulations, for instance as oral suspension and tablets. Different formulations and different amounts of Cefixime are provided for adult and pediatric patients for example as tablets comprising 200 mg and 400 mg Cefixime trihydrate and as oral suspension comprising 100 mg/5 ml Cefixime trihydrate.

From the point of view of bioavailability, the preferred form of administration of sparingly soluble medicaments such as beta lactam antibiotics is often an aqueous suspension. However, there are limitations associated with this form of administration. For example, as mentioned in the product insert of "Suprax", Cefixime, given orally, is about 40%-50% absorbed whether administered with or without food. The oral suspension, on the other hand, produces average peak concentrations approximately 25%-50% higher than the conventional tablets. The area under the time versus concentration curve is greater by approximately 10%-25% with the oral suspension than with the conventional tablet after doses of 100 to 400 mg, when tested in normal adult volunteers. Thus, at the same dosage strength, Cefixime tablets are not bioequivalent to the suspension. Although suspensions are the common mode of administration of Cefixime especially to the pediatric population, they suffer from other disadvantages such as limited shelf life and lack of accuracy of dose measurement. The bitter taste of many such medicaments is also a drawback. The bulky nature of the container often precludes ease of carriage and storage.

Thus, a need exists for developing a formulation of Cefixime, which does not suffer from the disadvantages of the suspension formulation as elaborated above.

Solid dosage forms that are swallowed such as tablets and capsules provide accurate dosage, avoid taste problems and are more amenable to being portable; but since they have to disintegrate in the gastrointestinal tract and the medicament has then to dissolve before it can be absorbed, absorption tends to be slower than from a suspension and may be less than complete leading to bioequivalence issues as pointed out earlier. Also, some patients have difficulty in swallowing tablets and capsules, and there is a practical limit to the size, and therefore the dose, that can be swallowed. This is particularly true for geriatric patients and children.

Thus, the challenge for us was to formulate a dosage form comprising Cefixime, which would have a bioavailability similar to that of a suspension comprising Cefixime, but without the attendant disadvantages of suspension.

SUMMARY OF THE INVENTION

It has surprisingly been found that pharmaceutical compositions comprising Cefixime trihydrate particles having a mean particle size between 20μ and 120μ exhibit higher bioavailability and are bioequivalent to suspension formulations comprising Cefixime trihydrate. Accordingly, the invention relates to a pharmaceutical composition comprising Cefixime trihydrate particles having a mean particle size between 20μ and 120μ as measured by Malvern light scattering, and a pharmaceutically acceptable excipient such that the formulation is bioequivalent to an already marketed oral suspension formulation comprising Cefixime trihydrate. The invention further provides a chewable tablet formulation of Cefixime comprising chewable base, sweetener and flavorants wherein the mean particle size of Cefixime particles is between 20μ and 120 μ.

DETAILED DESCRIPTION OF THE INVENTION

The present invention provides for a chewable tablet comprising Cefixime trihydrate particles having a mean particle size between 20μ and 120 μ.

The term Cefixime as used alone also denotes the trihydrate salt and the terms can be used interchangeably for the purpose of this invention.

The tablet is provided for in a range of strengths of Cefixime i.e. 100, 150, 200 and 300 mg of Cefixime as Cefixime trihydrate.

It is preferred that Cefixime particles have a mean particle size between 20μ and 120μ. The term "mean particle size between 20μ and 120μ" as used herein refers to Cefixime particles having a $d_{50}$ value between 20μ and 120μ. It is noted that the notation $d_x$ means that X % of particles have a diameter less than the specified diameter D. Thus, for example, a $d_{50}$ of 20μ for a particular sample of Cefixime means that 50% of the Cefixime particles in the said sample have a diameter less than 20 μ.

The term 'particles' refers to individual particles whether the particles exist singly or are agglomerated. Thus, a composition comprising Cefixime may contain agglomerates that are well beyond the size limit of about 120μ specified herein. However, if the mean particle size of the primary drug substance i.e. Cefixime trihydrate comprising the agglomerate is between 20μ and 120μ individually, then the agglomerate itself is considered to satisfy the particle size constraints defined herein and the composition is within the scope of the invention.

The said particle size limit for Cefixime may be achieved by any of the size reduction techniques known to those skilled in the art, for example, micronization, milling and the like.

Cefixime trihydrate is present in the desired dosage form from about 10% to about 50% by weight of the tablet.

The chewable tablet base in accordance with the present invention maybe selected from those commonly known in the art. For example, it is one or more selected from the group comprising xylitol, mannitol and sorbitol. It is present from about 25% to about 75% by weight of the tablet.

In addition to an excipient to provide a chewable base, the chewable tablet according to the present invention may optionally comprise further excipients for instance binders, disintegrants, lubricants, sweetening agents, coloring and flavoring agents.

Binders are present in from 1% to about 5% by weight of the tablet. Representative binders include low substituted hydroxypropyl cellulose, polyvinylpyrrolidone, pregelatinized starch and the like.

Disintegrants are present in from 1% to about 17% by weight of the tablet. Representative disintegrants include crospovidone, sodium starch glycolate, starches such as maize starch and dried starch, croscarmellose sodium and cellulose products such as microcrystalline cellulose, microfine cellulose, low substituted hydroxypropylcellulose, either used singly or in admixture.

Lubricants are present in from about 0.25% to about 6% by weight of tablet. Examples of lubricants include magnesium stearate, colloidal silicon dioxide and the like.

Sweetening agents are selected from amongst natural sweeteners such as sugars and artificial sweetening agents such as sodium saccharin or aspartame.

Flavoring agents include fruit flavours, which may be natural or synthetic.

Tablets of the present invention may be prepared by conventional techniques for example wet granulation, compaction or direct compression. In one process, granules are prepared by roller compaction and then milling from a primary blend comprising micronized Cefixime, Mannitol and about one third of the quantity of Magnesium stearate. The granules are then blended with the remaining ingredients and the remaining Magnesium stearate to form a secondary blend, which is then compressed into tablets. The invention is illustrated with following examples.

Example 1

| Ingredients | Quantity per tablet (mg) | Percent w/w |
|---|---|---|
| Cefixime trihydrate equivalent to Cefixime (micronized) | 360.86 | 30.07 |
| Mannitol DC | 602.44 | 50.20 |
| L-hydroxypropyl cellulose | 36.00 | 3.00 |
| Colloidal silicon dioxide | 6.00 | 0.50 |
| Crospovidone | 120.00 | 10.0 |
| Aspartame | 18.00 | 1.50 |
| Lake Colour Allura Red | 1.50 | 0.125 |
| Tutti Frutti flavor | 30.00 | 2.50 |
| Flavor Fantasy Permaseal | 6.00 | 0.50 |
| Magnesium stearate | 19.20 | 1.60 |
| Net tablet weight | 1200.00 | |

Brief Manufacturing Process:

Cefixime (micronized, $d_{50}$ between 20μ and 120μ) was sifted through a screen of appropriate aperture size. The other excipients were also subjected to a sifting process. Cefixime and Mannitol along with part quantity of Magnesium stearate were blended and compacted to get flakes. These flakes were sifted and milled to provide granules. The granules were admixed with the other excipients, lubricated and compressed to obtain tablets.

Example 2

| Ingredients | Quantity per tablet (mg) | Percent w/w |
|---|---|---|
| Cefixime trihydrate equivalent to Cefixime (micronized) | 241.30 | 30.16 |
| Mannitol DC | 400.90 | 50.11 |
| L-hydroxypropyl cellulose | 24.00 | 3.00 |
| Colloidal silicon dioxide | 4.00 | 0.50 |
| Crospovidone | 80.00 | 10.0 |
| Aspartame | 12.00 | 1.50 |
| Lake Colour Allura Red | 1.00 | 0.125 |
| Tutti Frutti flavor | 20.00 | 2.50 |
| Flavor Fantasy Permaseal | 4.00 | 0.50 |
| Magnesium stearate | 12.80 | 1.60 |
| Net tablet weight | 800.00 | |

Brief Manufacturing Process:

The same process was used as detailed in Example 1.

Example 3

| Ingredients | Quantity per tablet (mg) | Percent w/w |
|---|---|---|
| Cefixime trihydrate equivalent to Cefixime (micronized) | 120.65 | 30.16 |
| Mannitol DC | 200.45 | 50.11 |
| L-hydroxypropyl cellulose | 12.00 | 3.00 |
| Colloidal silicon dioxide | 2.00 | 0.50 |
| Crospovidone | 40.00 | 10.0 |
| Aspartame | 6.00 | 1.50 |
| Lake Colour Allura Red | 0.50 | 0.125 |
| Tutti Frutti flavor | 10.00 | 2.50 |
| Flavor Fantasy Permaseal | 2.00 | 0.50 |
| Magnesium stearate | 6.40 | 1.60 |
| Net tablet weight | 400.00 | |

Brief Manufacturing Process:

The same process was used as detailed in Example 1.

Example 4

| Ingredients | Quantity per tablet (mg) | Percent w/w |
|---|---|---|
| Cefixime trihydrate equivalent to Cefixime (micronized) | 114.32 | 45.73 |
| Mannitol DC | 100.43 | 40.00 |
| L-hydroxypropyl cellulose | 7.50 | 3.00 |
| Colloidal silicon dioxide | 1.25 | 0.50 |
| Crospovidone | 7.50 | 3.00 |
| Sodium saccharin | 3.00 | 1.20 |
| Lake of Sunset Yellow | 1.00 | 0.40 |
| Strawberry flavor | 7.50 | 3.00 |
| Flavor Fantasy Permaseal | 5.00 | 2.00 |
| Magnesium stearate | 2.50 | 1.00 |
| Net tablet weight | 250.00 | |

Brief Manufacturing Process:

The same process was used as detailed in Example 1.

Example 5

| Ingredients | Quantity per tablet (mg) | Percent w/w |
|---|---|---|
| Cefixime trihydrate equivalent to Cefixime (micronized) | 114.32 | 35.20 |
| Mannitol DC | 179.77 | 55.31 |
| L-hydroxypropyl cellulose | 9.75 | 3.00 |
| Colloidal silicon dioxide | 1.63 | 0.50 |
| Aspartame | 4.90 | 1.50 |
| Strawberry flavor | 9.75 | 3.00 |
| Magnesium stearate | 4.88 | 1.50 |
| Net tablet weight | 325.00 | |

Brief Manufacturing Process:

The same process was used as detailed in Example 1

Bioecuivalence Study

A bioequivalence study was carried out using the tablets comprising Cefixime having a mean particle size greater than 120μ and tablets comprising Cefixime having a mean particle size between 20μ and 120μ as prepared in Example 1 against the commercially available oral suspension "Suprax" using six healthy volunteers. The study was monitored in terms of the AUC and $C_{max}$ achieved with the test product and reference product. AUCs are plots of serum concentrations of Cefixime along the ordinate (Y-axis) against time on the abscissa (X-axis). Generally, the values for AUC represent a number of values taken from all the subjects in a population and are, therefore, mean values averaged over the entire population. $C_{max}$, the observed maximum in a plot of serum level concentration of Cefixime (Y-axis) versus time (X-axis) is likewise an average value.

Bioequivalence data for the chewable tablets comprising Cefixime having a mean particle size greater than 120μ, against the commercially available suspension formulation "Suprax" is shown below in Table 1.

Bioequivalence data for the chewable tablets comprising Cefixime having a mean particle size between 20μ and 120μ, against the commercially available suspension formulation "Suprax" is shown below in Table 2.

TABLE 1

BE fasting study data of Cefixime chewable tablets ($d_{50}$ greater than 120μ) against commercially available suspension formulation "Suprax":

| Test product: | Cefixime chewable tablets (300 mg) (Example 3) |
|---|---|
| Reference product: | Cefixime for Oral suspension, 100 mg/5 mL (Suprax) (15 mL) |

| Parameter | Cmax (mcg/mL) | AUC (0-t) (mcg · h/mL) |
|---|---|---|
| Test product (T) | 3.063 | 25.244 |
| Reference product (R) | 3.84 | 37.122 |
| T/R | 79.76 | 68.00 |

TABLE 2

BE fasting study data of Cefixime chewable tablets ($d_{50}$ between 20μ and 120μ) against commercially available suspension formulation "Suprax":

| Test product: | Cefixime chewable tablets (300 mg) (Example 3) |
|---|---|
| Reference product: | Cefixime for Oral suspension, 100 mg/5 mL (Suprax) (15 mL) |

| Parameter | Cmax (mcg/mL) | AUC (0-t) (mcg · h/mL) |
|---|---|---|
| Test product (T) | 3.789 | 29.673 |
| Reference product (R) | 3.715 | 28.837 |
| T/R | 100.7 | 101.6 |

As can be seen from the data above in Table 1, when the particle size of Cefixime was greater than 120μ, the T/R ratio for AUC for the chewable tablet was only 68% when compared to the suspension indicating that it is about 30% less bioavailable as compared to the suspension formulation. In contrast, surprisingly, a similar formulation comprising Cefixime with a mean particle size between 20μ and 120μ gave a T/R ratio for AUC of about 100% indicating that the chewable tablet in this case had bioavailability equal to that of the suspension formulation. A similar trend was noticed when the $C_{max}$ attained in both the cases was evaluated.

The embodiments of the invention in which an exclusive property or privilege is claimed are defined as follows:

1. A chewable tablet comprising granules embedded in a matrix of excipients, wherein the granules consist of Cefixime having a mean particle size between 20μ and 120μ, mannitol, and magnesium stearate,
   and the matrix of excipients comprising hydroxypropyl cellulose, crospovidone, magnesium stearate, and one or more fruit flavoring agents,
   wherein the chewable tablet comprises, in addition to the Cefixime:
   40-70 wt-% mannitol,
   1-5 wt-% hydroxypropyl cellulose,
   5-15 wt-% crospovidone; and
   2-5 wt-% one or more fruit flavoring agents,
   wherein said chewable tablet has a property that makes the tablet chewable by patients who have difficulty in swallowing tablets,
   wherein said chewable tablet when chewed and swallowed by a human being, shows AUC and Cmax that are substantially equivalent to that of a suspension of Cefixime.

2. The chewable tablet of claim 1, wherein the granules consist of 50 to 300 mg Cefixime.

3. The chewable tablet of claim 1, wherein the Cefixime is Cefixime trihydrate, and the Cefixime trihydrate is present in an amount from 10 to 50% by weight of the tablet.

4. The chewable tablet of claim 1, wherein the mannitol is present in an amount from 50 to 60% by weight of the tablet.

5. The chewable tablet of claim 1, further comprising a pharmaceutically acceptable excipient selected from the group consisting of lubricant, sweetening agent, and coloring agent.

6. The chewable tablet of claim 5, wherein the lubricant is selected from the group consisting of colloidal silicon dioxide and magnesium stearate.

7. The chewable tablet of claim 5, wherein the lubricant is present in an amount from 0.25 to 6% by weight of the tablet.

8. The chewable tablet of claim 5, wherein the sweetening agent is a natural or an artificial sweetening agent.

9. A chewable tablet comprising granules embedded in a matrix of excipients, wherein the granules consist of Cefixime having a mean particle size between 20μ and 120μ, mannitol, and magnesium stearate,
and the matrix of excipients comprising hydroxypropyl cellulose, crospovidone, magnesium stearate, and one or more fruit flavoring agents,
wherein the chewable tablet comprises, in addition to the Cefixime:
40-70 wt-% mannitol,
1-5 wt-% hydroxypropyl cellulose,
5-15 wt-% crospovidone; and
2-5 wt-% one or more fruit flavoring agents.

10. The chewable tablet of claim 9, wherein the granules consist of 50 to 300 mg Cefixime.

11. The chewable tablet of claim 9, wherein the Cefixime is Cefixime trihydrate, and the Cefixime trihydrate is present in an amount from 10 to 50% by weight of the tablet.

12. The chewable tablet of claim 9, wherein the mannitol is present in an amount from 50 to 60% by weight of the tablet.

13. The chewable tablet of claim 9, further comprising a pharmaceutically acceptable excipient selected from the group consisting of lubricant, sweetening agent, and coloring agent.

14. The chewable tablet of claim 13, wherein the lubricant is selected from the group consisting of colloidal silicon dioxide and magnesium stearate.

15. The chewable tablet of claim 13, wherein the lubricant is present in an amount from 0.25 to 6% by weight of the tablet.

16. The chewable tablet of claim 13, wherein the sweetening agent is a natural or an artificial sweetening agent.

* * * * *